(12) United States Patent
Hegstrom

(10) Patent No.: US 10,161,879 B1
(45) Date of Patent: Dec. 25, 2018

(54) MEASUREMENT OF THICKNESS, SURFACE PROFILE, AND OPTICAL POWER OF A TRANSPARENT SHEET

(71) Applicant: Eric Hegstrom, Tucson, AZ (US)

(72) Inventor: Eric Hegstrom, Tucson, AZ (US)

(73) Assignee: LiteSentry Corporation, Northfield, MN (US)

( * ) Notice: Subject to any disclaimer, the term of this patent is extended or adjusted under 35 U.S.C. 154(b) by 0 days.

(21) Appl. No.: 15/662,311

(22) Filed: Jul. 28, 2017

(51) Int. Cl.
*G01B 7/06* (2006.01)
*G01N 21/896* (2006.01)
*G01B 11/30* (2006.01)
*G01N 21/958* (2006.01)

(52) U.S. Cl.
CPC ............. *G01N 21/896* (2013.01); *G01B 7/06* (2013.01); *G01B 11/306* (2013.01); *G01N 21/958* (2013.01)

(58) Field of Classification Search
CPC ...... G02B 2027/012; G02B 2027/0121; G02B 26/127; G02B 27/01; G02B 27/0101; G02B 27/28; G02B 5/3058; G02B 7/005; G02B 13/16; G02B 13/18; G02B 19/0028; G02B 19/0042; G02B 1/10
See application file for complete search history.

(56) References Cited

U.S. PATENT DOCUMENTS 7,345,698 B2 * 3/2008 Abbott ................. G01B 11/306
348/86

* cited by examiner

*Primary Examiner* — Michael P Stafira
(74) *Attorney, Agent, or Firm* — Edward Weck

(57) ABSTRACT

This present invention relates to an apparatus and method for measuring the profile and reflective optical power of one or more surfaces of transparent sheets and transmissive optical power and thickness of one or more transparent sheets at a plurality of locations over the complete transparent sheet. The measurement results are presented to a user graphically and all data is stored for further processing, process control, and quality assurance.

14 Claims, 5 Drawing Sheets

31

MEASUREMENT OF THICKNESS, SURFACE PROFILE, AND OPTICAL POWER OF A TRANSPARENT SHEET

BACKGROUND OF THE INVENTION

Summary of the Invention

The present invention relates to an apparatus and method for measuring the profile and reflective optical power of one or more surfaces of transparent sheets and transmissive optical power and thickness of one or more transparent sheets at a plurality of locations over the complete sheet.

Description of the Related Art

U.S. Pat. No. 7,345,698 (Abbott and Hegstrom) discloses a method to measure surface reflected optical distortion from a transparent sheet with a series of filled strips or filled shapes ("filled targets") such as circles, see FIG. 2. A major weakness of using filled targets for analyzing reflected images from multiple surfaces of transparent sheets, is that the reflected images from multiple surfaces overlap and it is impossible to reliably discriminate which part of the reflection is from which surface, see FIG. 4). This means the reflected image does not show an individual shape from each discrete surface but instead a "composite measure" of the combined multiple surface reflections. In addition, in the prior art, the transparent sheet must also be assumed to be of a uniform and constant thickness for distortion measurements. This is because the reflected composite measurement that encompasses the reflection of the filled targets grows as the surfaces become further apart (in the case of a single transparent sheet, a thicker sheet will create a larger composite image of the target reflections off of multiple surfaces). To compensate for this, the prior art requires an independent source of the surface spacing measurement, which is simply the sheet thickness in the case of a single transparent sheet. This spacing data needs to be provided by the operator or by a separate, often expensive, thickness sensor.

Furthermore, in the prior art it is impossible to measure distortion very near the edge of the transparent sheet. This is because it is impossible to reliably determine whether the reflection of a solid target is: 1) changing in size and shape due to optical distortion or, 2) being truncated by the edge of the transparent sheet, see FIG. 6. Therefore all reflected images near the edge of the transparent sheet must be ignored and measurements are only considered valid if they are a significant distance (usually a single target size) from the edge of the transparent sheet. Furthermore, as the prior art invention does not discriminate between the reflected images from each surface, it is unable to provide any information about how the surfaces interact and is therefore unable to provide a measurement of transmissive optical power. In the case of a single transparent sheet, the optical properties can be modeled as a simple lens allowing the application of well know optical formulas such as the lensmaker's equation to solve for transmissive power and/or focal length.

SUMMARY OF THE INVENTION

Apparatus and methods in accordance with the present invention may resolve many of the needs and shortcomings discussed above and will provide additional improvements and advantages as will be recognized by those skilled in the art upon review of the present disclosure.

Novel lighting and imaging design of the present improvement allows measurement and determination of reflective optical power (also known as distortion in diopters) without the need for a thickness measurement (or input). This simplifies the system and lowers the cost. Further, the invention improves accuracy of measurements on a wide range of glass thicknesses, making measurement thickness independent. The invention also allows measurement much nearer to the edges of the sheet than possible with the prior art. This invention may be used in the control of tempering or laminating processes.

This invention uses a target image (an "outline target", FIGS. 3A, 3B) that has a relatively thin outline thickness, typically 2-20% of the target width. The outline targets may be either: dark in color with a contrasting background being light in color, FIG. 3A; or light in color with the contrasting background being dark in color, FIG. 3B. Unlike the filled targets used in the prior art invention (FIG. 2), the individual reflected image of the outline target from each of multiple surfaces can easily be discriminated and therefore the profile of each surface can be computed independently (FIGS. 4 and 5). The use of outline targets in this improvement is superior to the use of filled targets in the prior art because the line defining the outline target is thin enough so that, given a sufficient angle between the camera and outline target, the apparent offset between reflected images from multiple surfaces will be wider than the outline thickness of the outline target. Since the apparent offset is larger than the outline thickness of the outline target there will be an area with no target reflection between neighboring surface reflections. This area with no target reflection is easily identified, measured and analyzed in software using standard computer vision algorithms. The ability to measure multiple surfaces separately allows the computation of transmissive optical power. Additionally, unlike in the case of the filled target taught by the prior art (FIG. 6), it is very easy to determine if the edge of the transparent sheet truncates the reflected image of an outline target since it will no longer appear to be a complete closed feature (FIG. 7). The filled target is self-verifying (FIG. 7) in that if the complete closed figure is observed, it is known that the measurement is one on which one can rely (it is reliable). Measurements can be relied upon, or are reliable, if there is a complete closed figure, which is assured if the closed figure is within the outline width of the edge.

BRIEF DESCRIPTION OF THE DRAWINGS

All Figures are illustrated for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

DETAILED DESCRIPTION OF THE INVENTION

Figure 5:
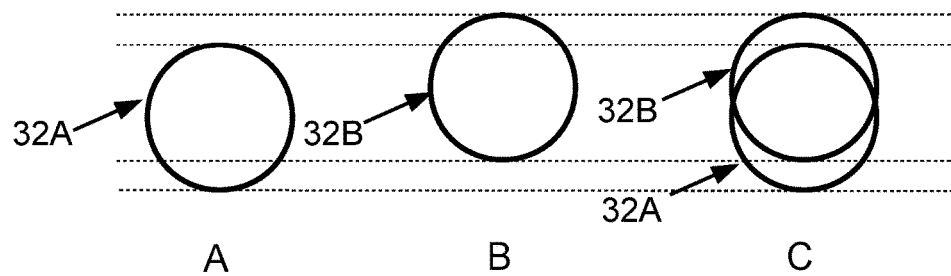
FIGS. 5A, 5B and 5C of the drawings show diagrams of reflections of outline targets.

This invention describes an improved apparatus and methods for measuring optical distortion in a transparent sheet, the apparatus (FIGS. 1A, 1B) comprising:

a conveyor 13 receiving and positioning the transparent sheet 11;

a light source 15 mounted on a first side of the conveyor 13, the light source 15 projecting a plurality of two-dimensional images 31 across the width of the conveyor 13 wherein the plurality of two-dimensional images 31 appear continuously and simultaneously on the transparent sheet 11, with each of the plurality of two-dimensional images 31 separated from all others of the plurality of two-dimensional images 31 by a background, with each of the plurality of two-dimensional images 31 regularly spaced from each adjacent one of the plurality of two-dimensional images 31, a camera 18 oriented to continuously and simultaneously detect a plurality of reflected two-dimensional images corresponding to the plurality of two-dimensional images; and a processing circuit 20 coupled to receive output data from the camera 18 to measure magnification and orientation of each of the plurality of reflected two-dimensional images and compute lens power based on a measurement of magnification of the reflected two-dimensional images, wherein the lens power is indicative of a local curvature of the transparent sheet over the width of the conveyor 13, with the improvement being that the plurality of two-dimensional images (FIGS. 3,5,7 and 8) are not completely filled 32 and are dark in color and the background is light in color or the plurality of two dimensional images 32 are not completely filled and are light in color and the background is dark in color, and with the additional improvement being that the processing circuit will also compute transmissive optical power by computing the optical interaction of the local curvatures of the multiple surfaces (FIG. 5).

The improved apparatus wherein each of the plurality of two-dimensional images which are not completely filled 32 are filled a fraction of an outline thickness 33 of a completely filled two-dimensional image.

The improved apparatus wherein the fraction of the outline thickness 33 is less than 10%, less than 5%, less than 1% or less than 0.1% of the completely filled two-dimensional image 31.

The improved apparatus wherein each of the plurality of two-dimensional images which are not completely filled 32 are filled less than 60%, less than 50%, less than 40%, less than 30%, less than 20%, less than 10%, less than 5%, less than 2%, less than 1% or less than 0.5% of a completely filled two-dimensional image.

The improved apparatus wherein a measured relative location of each of the plurality of reflected not completely filled two-dimensional images 32 from two or more surfaces (FIG. 5) is used to compute a thickness of the transparent sheet (FIGS. 8A, 8B and 8C).

The improved apparatus wherein the thickness of the transparent sheet is not input from an external thickness sensor 19 and is not input by an operator of the apparatus.

The improved apparatus wherein the transparent sheet 11 may be determined to have a thickness between 0.1 mm and 50 mm.

The improved apparatus wherein the plurality of not completely filled two-dimensional images 32 are between 5 mm and 60 mm in diameter.

The improved apparatus wherein each of the plurality of not completely filled two-dimensional images 32 are separated from a nearest not completely filled two-dimensional image 32 by from 0.1 mm to 100 mm.

The improved apparatus wherein the plurality of reflected two-dimensional images 32 from the transparent sheet 11 at an edge of the transparent sheet are not closed two-dimensional images 31 but are truncated two dimensional images 35, which may be ignored for computing transmissive optical power and allows distortion measurement up to the edge of the transparent sheet 11.

This invention describes an improved method of measuring optical distortion in a transparent sheet 11, the method comprising:

receiving and positioning the transparent sheet 11 with a conveyor 13;

projecting light from a light source 15 mounted on a first side of the conveyor 13, the light source 15 projecting a plurality of two-dimensional images 31 across the width of the conveyor 13 wherein the plurality of two-dimensional images 31 appear continuously and simultaneously on the transparent sheet 11, with each of the plurality of two-dimensional images 31 separated from all others of the plurality of two-dimensional images 31 by a background, with each of the plurality of two-dimensional images 31 regularly spaced from each adjacent one of the plurality of two-dimensional images 31, detecting a plurality of reflected two-dimensional images corresponding to the plurality of two-dimensional images 31 with a camera oriented to continuously and simultaneously; and receiving output data in a processing circuit 20 coupled to the camera 18 and measuring magnification and orientation of each of the plurality of reflected two-dimensional images and computing lens power based on measuring of magnification of the reflected two-dimensional images, wherein the lens power is indicative of a local curvature of the transparent sheet over the width of the conveyor, with the improvement being projecting the plurality of two-dimensional images which are not completely filled and are dark in color and the background is light in color or the plurality of two dimensional images which are not completely filled and are light in color and the background is dark in color, with the additional improvement being computing with the processing circuit the transmissive optical power by computing the optical interaction of the local curvatures of the multiple surfaces (FIG. 5).

The improved method wherein the projecting of the plurality of two-dimensional images which are not completely filled 32, are filled a fraction of an outline thickness of a completely filled two-dimensional image.

The improved method wherein the fraction of the outline thickness 33 is less than 10%, less than 5%, less than 1% or less than 0.1% of the completely filled two-dimensional image.

The improved method wherein the projecting of each of the plurality of two-dimensional images which are not completely filled 32 are filled less than 60%, less than 50%, less than 40%, less than 30%, less than 20%, less than 10%, less than 5%, less than 2%, less than 1% or less than 0.5% of a completely filled two-dimensional image.

The improved method wherein measuring a relative location of each of the plurality of reflected not completely filled two-dimensional images 32 from two or more surfaces (FIG. 5) is used to compute a thickness of the transparent sheet 11.

The improved method wherein the defining the thickness of the transparent sheet 11 does not require inputting from an external sensor or inputting by an operator of the apparatus.

The improved method wherein the defining the thickness of the transparent sheet 11 may be between a thickness between 0.1 mm and 50 mm.

The improved method wherein the projecting the plurality of not completely filled two-dimensional images 32, the plurality of not completely filled two-dimensional images 32 are between 5 mm and 60 mm in diameter.

The improved method wherein the projecting the each of the plurality of not completely filled two-dimensional images 32, the not completely filled two-dimensional images 32 are separated from a nearest two-dimensional image by from 0.1 mm to 100 mm.

The improved method wherein the measuring of the reflected not completely filled two-dimensional images 32 from the transparent sheet 11 at an edge of the transparent sheet does not show closed two-dimensional images 32 but shows truncated two-dimensional images 35, which may be ignored for computing transmissive optical power and allows reliable distortion measurement up to the edge of the transparent sheet 11.

PREFERRED EMBODIMENT

Figure 9:
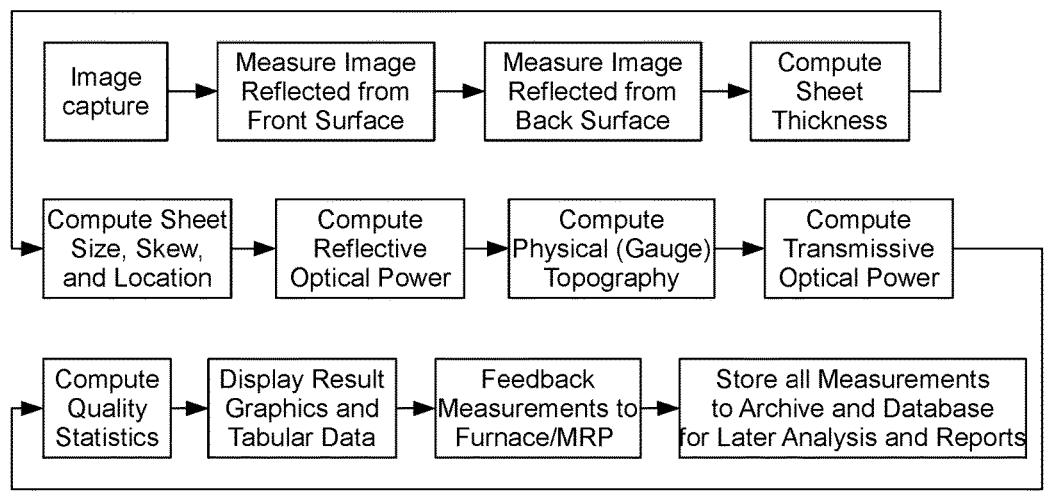
FIG. 9 of the drawings shows a block diagram of the processing software.

The invention provides a new and unique patterned image 32 for measuring optical distortion in a transparent sheet 11. The invention consists of a plurality of outline targets (not completely filled two-dimensional images or closed two-dimensional images) 32 (FIGS. 3A, 3B) above or adjacent to a line of moving transparent sheets 11 (see FIGS. 1 and 2). Any shape of target, such as polygons, can be used, although a circle is used in the preferred embodiment. The plurality of outline targets 32 (see FIGS. 3A, 3B) are illuminated (either from the front or back). The plurality of outline targets 32 are dark in color and the background is white or light in color. One or more imaging devices 18 (typically CCD or CMOS cameras) is aimed to view the reflections of the outline targets 32 across the width of the transparent sheet 11. The angle α (FIG. 1A) between the outline targets 32 and the camera 18 is sufficiently large to allow discrimination of the images from each surface (FIG. 5). The angle α may be between one (1) and forty-five (45) degrees but in the preferred embodiment is fifteen (15) degrees. Images are captured at fixed distances along the transparent sheet 11 as the transparent sheet 11 is conveyed with respect to the imaging device 18. Typically an encoder 12 is coupled to the conveyor 13 and the encoder signal is used to trigger the image capture at a predefined distance interval. The software measures the size and shape of the reflected image and compares that to a known calibration standard and generates reflected optical power maps of all surfaces (FIGS. 5A, 5B, 5C). Furthermore the relative positions of the images from multiple surfaces (FIGS. 5A, 5B, 5C) can be used to compute the spacing between those surfaces (FIGS. 5A, 5B, 5C). In the case of a single transparent sheet 11 this translates to sheet thickness (FIG. 9). In addition, by analyzing the optical interaction of the individual surface profiles of these multiple surfaces (FIGS. 5A, 5B, 5C) the transmissive optical power may be computed for each of the plurality of locations on the surface of the transparent sheet 11. The results of all these measurements are displayed in false colored graphical form overlaid on an outline of the transparent sheet 11. Furthermore statistical summaries of these measurements are displayed in a table. All raw data and statistical summaries are saved to files for audit and analysis. Quality and process parameters can be set and failing parts are flagged and process feedback is output to the tempering control system.

This invention also discloses a method to measure the distance between surfaces (FIG. 5) by comparing the displacement of the reflection location with a known standard. In the case of a single sheet, the thickness of the sheet is indicated by the apparent separation of the images reflected by the front surface and back surface (FIGS. 5A, 5B and 5C). The image separation distance can be correlated with known values to compute the sheet thickness in millimeters or inches. FIG. 8A illustrates a sheet thickness of 2 mm, FIG. 8B represents a sheet thickness of 6 mm and FIG. 8C represents a sheet thickness of 25 mm.

Figure 1A:
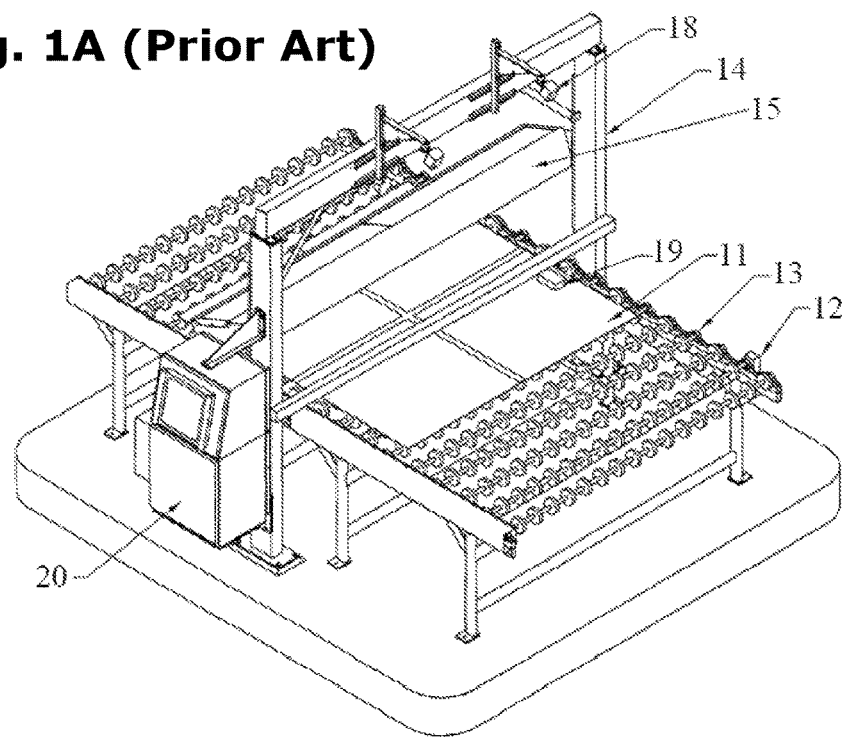
FIGS. 1A and 1B of the drawings show side views of an apparatus for inspecting individual transparent sheets (prior art).

FIG. 1A shows the prior art apparatus (U.S. Pat. No. 7,345,698) for inspecting individual transparent sheets 11 which have been treated by a glass tempering system. A conventional encoding device or encoder 12, detects the movement of the transparent sheets 11 on the conveyor 13 based upon the rotation of one of the rollers of a conveyor 13. The apparatus includes a support frame 14 and a light box 15 having a set of light bulbs 16 and a patterned diffuser 17. The image capture CCD cameras 18 apply output signals to a high-speed processor 20 that executes algorithms to process the data.

Figure 1B:
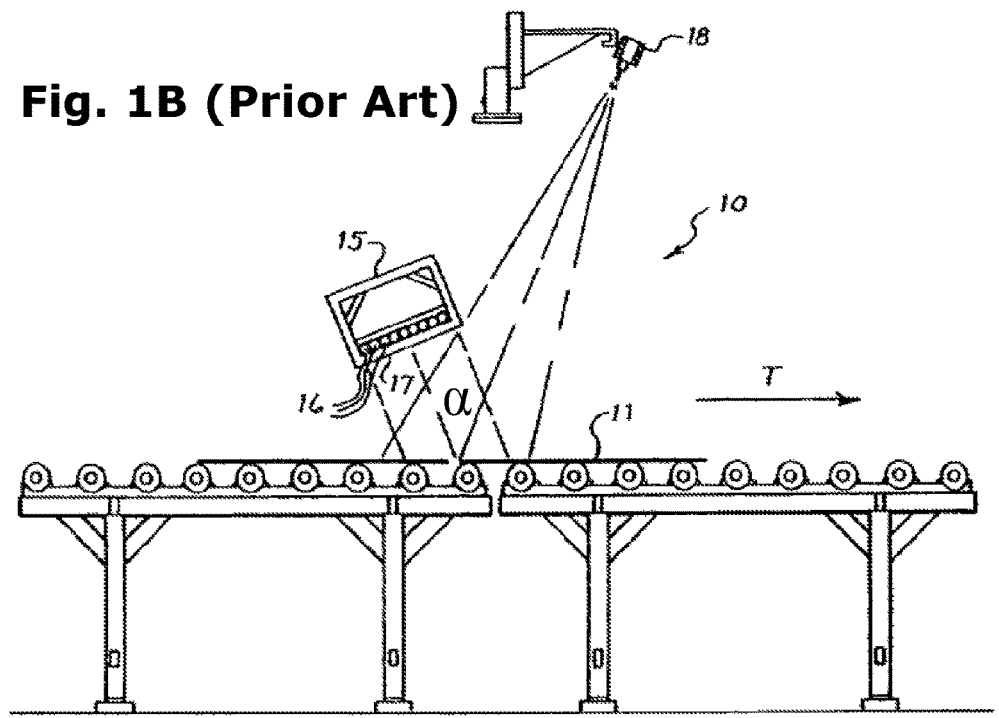

FIG. 1B shows the prior art invention (U.S. Pat. No. 7,345,698) where glass sheets 11 are conveyed under the light box 15 and diffuser 17, and the patterned image (see FIG. 2A) is projected onto and reflected from the surfaces of the transparent sheets 11. The reflected image is captured by the CCD cameras 18. The transport direction is indicated by the arrow T. In a preferred embodiment the angle α, between camera and the outline target, is fifteen (15) degrees.

Figure 2:
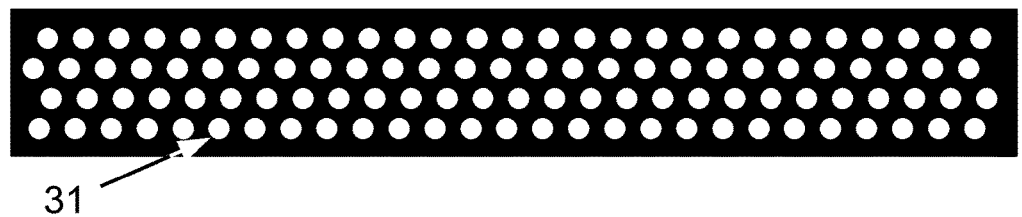
FIG. 2 of the drawings shows a top view of a plurality of filled targets (prior art).
Figure 3A:
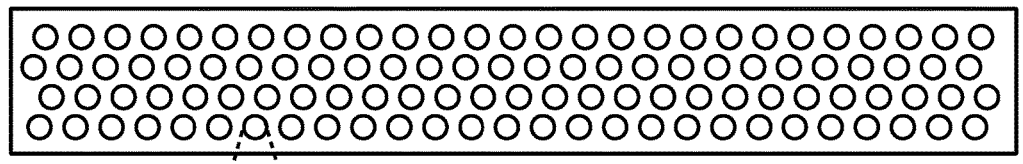
FIGS. 3A and 3B of the drawings shows top views of a plurality of outline targets.
Figure 3A:
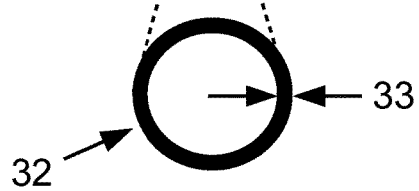
Figure 3B:
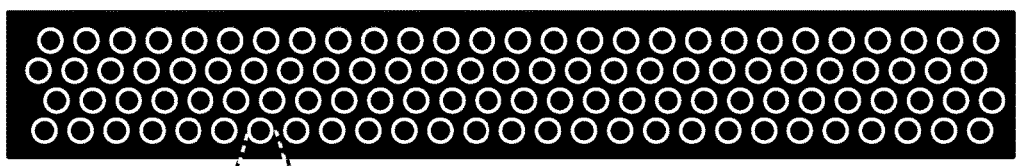
Figure 3B:
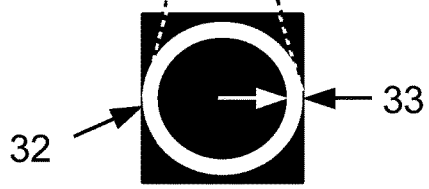

FIG. 2 shows a plurality of reflections of filled targets 31 from a transparent sheet 11 (prior art). FIGS. 3A and 3B shows a plurality of reflections of outline targets (not completely filled two dimensional images) 32 from a transparent sheet 11. FIG. 3A. shows the plurality of two-dimensional images 32 which are not completely filled and are dark in color and the background is light in color and FIG. 3B shows the plurality of two dimensional images which are not completely filled 32 and are light in color and the background is dark in color. FIGS. 3A and 3B also show the outline thickness 33 of the plurality of two-dimensional images 32 which are not completely filled.

Figure 4:
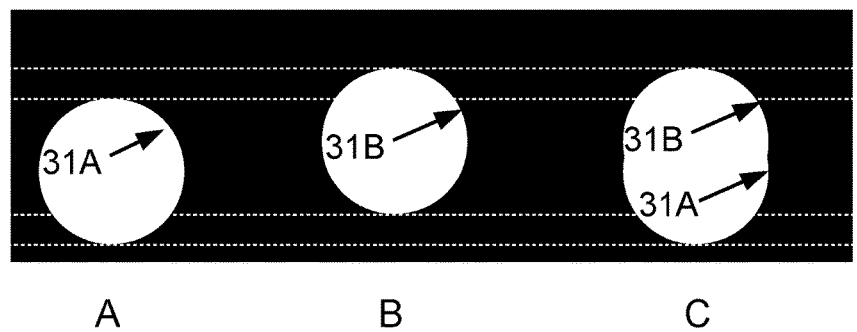
FIGS. 4A, 4B and 4C of the drawings show diagrams of reflections of filled targets (prior art).

FIG. 4A shows a filled target reflection 31A only from a front surface of a transparent sheet 11, FIG. 4B shows a filled target reflection 31B only from a back surface of a transparent sheet 11 and FIG. 4C shows reflections (31A, 31B) from both the front surface and the back surface of the transparent sheet 11. The dotted lines compare the vertical offset of the filled target reflection 31A and filled target reflection 31B. FIG. 5A shows an outline target reflection 32A from a front surface of a transparent sheet 11, FIG. 5B shows an outline target reflection 32B from a back surface of a transparent sheet 11 and FIG. 5C shows outline target reflections (32A, 32B) from both the front surface and the back surface of the transparent sheet 11. The dotted lines compare the vertical offset of the outline target reflection 32A and outline target reflection 32B. The use of outline targets 32 makes it easier to reliably discriminate the outline target reflection (32A, 32B) of the front surface from that of the back surface.

Figure 6:
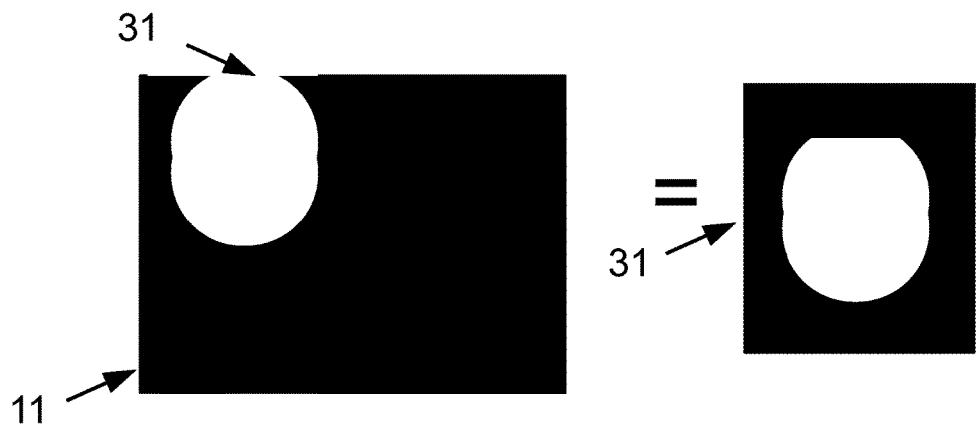
FIG. 6 of the drawings shows a diagram of a reflection of a filled target near the edge of a transparent sheet (prior art).
Figure 7:
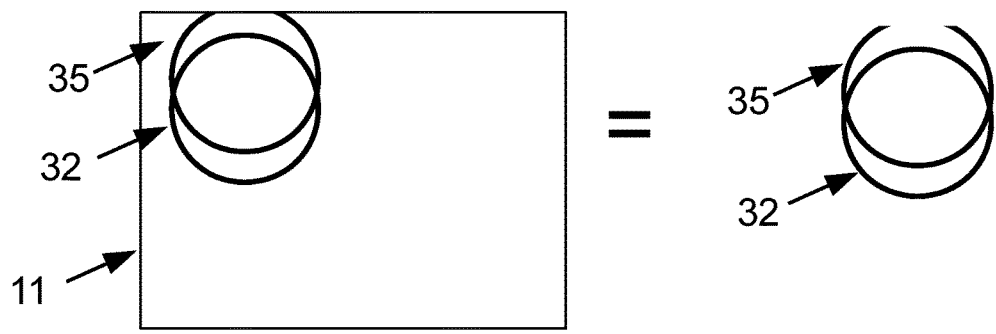
FIG. 7 of the drawings shows a diagram of a reflection of an outline target near the edge of a transparent sheet.
Figure 8:
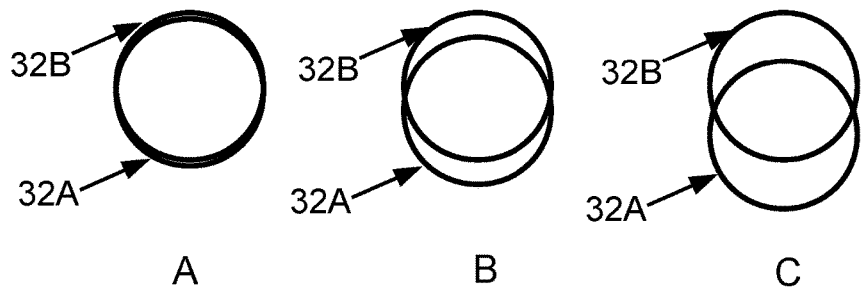
FIG. 8 of the drawings shows a diagram of how transparent sheet thickness is determined.

FIG. 6 shows a reflection of a filled target 31 near the edge of a transparent sheet 11 (prior art). FIG. 7 shows a reflection of an outline target 32 near the edge of a transparent sheet 11 producing a truncated image 35, which allows reliable measurement much nearer to the edge of the transparent sheet.

FIGS. 8A, 8B and 8C show an outline target reflection 32A from a front surface of a transparent sheet 11 and an outline target reflection 32B from a back surface of a transparent sheet 11. The reflections 32A and 32B vary with the thickness of the transparent sheet 11: 2 mm thickness (FIG. 8A), 6 mm thickness (FIG. 8B) and 25 mm thickness (FIG. 8C).

FIG. 9 of the drawings shows a block diagram of the processing and analysis steps for measuring a single transparent sheet. The processing and analysis steps include: image capture; measure the image reflected from the front surface; measure the image reflected from the back surface; compute sheet thickness; compute sheet size skew and location; compute reflective optical power; compute physical (gauge) topography; compute transmissive optical power; compute quality statistics; display result graphics and tabular data; feedback measurements to furnace/MRP; and store all measurements to archive and database for later analysis and reports.

The foregoing discussion discloses and describes merely exemplary embodiments of the present invention. The invention is not limited to the method and the object as described in detail above. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An improvement of an apparatus for measuring optical distortion in a transparent sheet, the apparatus comprising:
    a conveyor receiving and positioning the transparent sheet;
    a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images,
    a camera oriented to continuously and simultaneously detect a plurality of reflected two-dimensional images; and
    a processing circuit coupled to receive output data from the camera to measure magnification and orientation of each of the plurality of reflected two-dimensional images and compute lens power based on a measurement of magnification of the reflected two-dimensional images, wherein the lens power is indicative of a local curvature of the transparent sheet over the width of the conveyor,
    with the improvement being that the plurality of two-dimensional images are not completely filled and the two-dimensional images and the background are of contrasting colors, and with the additional improvement being that the processing circuit will also compute transmissive optical power by computing the optical interaction of the local curvatures of the multiple surfaces wherein each of the plurality of two-dimensional images which are not completely filled, are filled a fraction of an outline thickness of a completely filled two-dimensional image.

2. The improvement of claim 1 wherein the fraction of the outline thickness is less than 10%, less than 5%, less than 1% or less than 0.1% of the completely filled two-dimensional image.

3. An improvement of an apparatus for measuring optical distortion in a transparent sheet, the apparatus comprising:
    a conveyor receiving and positioning the transparent sheet;
    a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images,
    a camera oriented to continuously and simultaneously detect a plurality of reflected two-dimensional images; and
    a processing circuit coupled to receive output data from the camera to measure magnification and orientation of each of the plurality of reflected two-dimensional images and compute lens power based on a measurement of magnification of the reflected two-dimensional images, wherein the lens power is indicative of a local curvature of the transparent sheet over the width of the conveyor,
    with the improvement being that the plurality of two-dimensional images are not completely filled and the two-dimensional images and the background are of contrasting colors, and with the additional improvement being that the processing circuit will also compute transmissive optical power by computing the optical interaction of the local curvatures of the multiple surfaces,
    wherein each of the plurality of two-dimensional images which are not completely filled are filled less than 60%, less than 50%, less than 40%, less than 30%, less than 20%, less than 10%, less than 5%, less than 2%, less than 1% or less than 0.5% of a completely filled two-dimensional image.

4. An improvement of an apparatus for measuring optical distortion in a transparent sheet, the apparatus comprising:
    a conveyor receiving and positioning the transparent sheet;

a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images, a camera oriented to continuously and simultaneously detect a plurality of reflected two-dimensional images; and a processing circuit coupled to receive output data from the camera to measure magnification and orientation of each of the plurality of reflected two-dimensional images and compute lens power based on a measurement of magnification of the reflected two-dimensional images, wherein the lens power is indicative of a local curvature of the transparent sheet over the width of the conveyor, with the improvement being that the plurality of two-dimensional images are not completely filled and the two-dimensional images and the background are of contrasting colors, and with the additional improvement being that the processing circuit will also compute transmissive optical power by computing the optical interaction of the local curvatures of the multiple surfaces wherein a measured relative location of each of the plurality of reflected not completely filled two-dimensional images from two or more surfaces is used to compute a thickness of the transparent sheet.

5. The improvement of claim 4 wherein the thickness of the transparent sheet is not input from an external thickness sensor and is not input by an operator of the apparatus.

6. The improvement of claim 5 wherein the transparent sheet may be determined to have a thickness between 0.1 mm and 50 mm.

7. An improvement of an apparatus for measuring optical distortion in a transparent sheet, the apparatus comprising:

a conveyor receiving and positioning the transparent sheet;

a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images, a camera oriented to continuously and simultaneously detect a plurality of reflected two-dimensional images; and a processing circuit coupled to receive output data from the camera to measure magnification and orientation of each of the plurality of reflected two-dimensional images and compute lens power based on a measurement of magnification of the reflected two-dimensional images, wherein the lens power is indicative of a local curvature of the transparent sheet over the width of the conveyor, with the improvement being that the plurality of two-dimensional images are not completely filled and the two-dimensional images and the background are of contrasting colors, and with the additional improvement being that the processing circuit will also compute transmissive optical power by computing the optical interaction of the local curvatures of the multiple surfaces wherein the plurality of reflected two-dimensional images from the transparent sheet at an edge of the transparent sheet are not closed two-dimensional images but are truncated two dimensional images, which may be ignored for computing transmissive optical power and allows reliable distortion measurement up to the edge of the transparent sheet.

8. An improvement of a method measuring optical distortion in a transparent sheet, the method comprising:

receiving and positioning the transparent sheet with a conveyor;

projecting light from a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images, detecting with a camera the plurality of reflected two-dimensional images continuously and simultaneously; and receiving output data in a processing circuit coupled to the camera and measuring magnification and orientation of each of the plurality of reflected two-dimensional images and computing lens power based on measuring of magnification of the reflected two-dimensional images, wherein the lens power is indicative of a local curvature of the transparent sheet over the width of the conveyor, with the improvement being projecting the plurality of two-dimensional images which are not completely filled and are of a contrasting color with the background and with the additional improvement being computing with the processing circuit the transmissive optical power by computing the optical interaction of the local curvatures of the multiple surfaces wherein the projecting of the plurality of two-dimensional images which are not completely filled, are filled a fraction of an outline thickness of a completely filled two-dimensional image.

9. The improvement of claim 8 wherein the fraction of the outline thickness is less than 10%, less than 5%, less than 1% or less than 0.1% of the completely filled two-dimensional image.

10. An improvement of a method measuring optical distortion in a transparent sheet, the method comprising:

receiving and positioning the transparent sheet with a conveyor;

projecting light from a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images, detecting with a camera the plurality of reflected two-dimensional images continuously and simultaneously; and receiving output data in a processing circuit coupled to the camera and measuring magnification and orientation of each of the plurality of reflected two-dimensional images and computing lens power based on measuring of magnification of the reflected two-dimensional images, wherein the lens power is indicative of a local curvature of the transparent sheet over the width of the conveyor, with the improvement being projecting the plurality of two-dimensional images which are not completely filled and are of a contrasting color with the background and with the additional improvement being computing with the processing circuit the transmissive optical power by computing the optical interaction of the local curvatures of the multiple surfaces wherein the projecting of each of the plurality of two-dimensional images which are not completely filled are filled less than 60%, less than 50%, less than 40%, less than 30%, less than 20%, less than 10%, less than 5%, less than 2%, less than 1% or less than 0.5% of a completely filled two-dimensional image.

11. An improvement of a method measuring optical distortion in a transparent sheet, the method comprising:
receiving and positioning the transparent sheet with a conveyor;
projecting light from a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images, detecting with a camera the plurality of reflected two-dimensional images continuously and simultaneously; and receiving output data in a processing circuit coupled to the camera and measuring magnification and orientation of each of the plurality of reflected two-dimensional images and computing lens power based on measuring of magnification of the reflected two-dimensional images, wherein the lens power is indicative of a local curvature of the transparent sheet over the width of the conveyor, with the improvement being projecting the plurality of two-dimensional images which are not completely filled and are of a contrasting color with the background and with the additional improvement being computing with the processing circuit the transmissive optical power by computing the optical interaction of the local curvatures of the multiple surfaces wherein measuring a relative location of each of the plurality of reflected not completely filled two-dimensional images from two or more surfaces is used to compute a thickness of the transparent sheet.

12. The improvement of claim 11 wherein the defining the thickness of the transparent sheet does not require inputting from an external sensor or inputting by an operator of the apparatus.

13. The improvement of claim 12 wherein the defining the thickness of the transparent sheet may be between a thickness between 0.1 mm and 50 mm.

14. An improvement of a method measuring optical distortion in a transparent sheet, the method comprising:
receiving and positioning the transparent sheet with a conveyor;
projecting light from a light source mounted on a first side of the conveyor, the light source projecting a plurality of two-dimensional images across the width of the conveyor wherein the plurality of two-dimensional images appear continuously and simultaneously on the transparent sheet, with each of the plurality of two-dimensional images separated from all others of the plurality of two-dimensional images by a background, with each of the plurality of two-dimensional images regularly spaced from each adjacent one of the plurality of two-dimensional images, detecting with a camera the plurality of reflected two-dimensional images continuously and simultaneously; and receiving output data in a processing circuit coupled to the camera and measuring magnification and orientation of each of the plurality of reflected two-dimensional images and computing lens power based on measuring of magnification of the reflected two-dimensional images, wherein the lens power is indicative of a local curvature of the transparent sheet over the width of the conveyor, with the improvement being projecting the plurality of two-dimensional images which are not completely filled and are of a contrasting color with the background and with the additional improvement being computing with the processing circuit the transmissive optical power by computing the optical interaction of the local curvatures of the multiple surfaces wherein the measuring the reflected two-dimensional images from the transparent sheet at an edge of the transparent sheet does not show closed two-dimensional images but shows truncated two-dimensional images, which may be ignored for computing transmissive optical power and allows reliable distortion measurement up to the edge of the transparent sheet.

* * * * *